United States Patent
Lindner et al.

(10) Patent No.: US 8,653,321 B2
(45) Date of Patent: Feb. 18, 2014

(54) METHOD FOR DETERMINING THE GEL STRENGTH OF A HYDROGEL

(75) Inventors: Torsten Lindner, Kronberg (DE); Matthias Morand, Bad Soden (DE); Axel Meyer, Frankfurt (DE); Maik Tremel, Schwalbach (DE); Michael Rene Weaver, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 509 days.

(21) Appl. No.: 13/035,091

(22) Filed: Feb. 25, 2011

(65) Prior Publication Data

US 2011/0203355 A1     Aug. 25, 2011

Related U.S. Application Data

(60) Provisional application No. 61/308,026, filed on Feb. 25, 2010.

(51) Int. Cl.
*A61F 13/20* (2006.01)
*G01B 5/30* (2006.01)

(52) U.S. Cl.
USPC .............. 604/368; 604/367; 428/327; 73/760

(58) Field of Classification Search
USPC ................. 604/367–372; 428/327; 73/760
See application file for complete search history.

(56) References Cited

U.S. PATENT DOCUMENTS

| | | |
|---|---|---|
| 3,661,875 A | 5/1972 | Sieja |
| 4,062,817 A | 12/1977 | Westerman |
| 4,076,663 A | 2/1978 | Masuda et al. |
| 4,093,776 A | 6/1978 | Aoki et al. |
| 4,625,001 A | 11/1986 | Tsubakimoto et al. |
| 4,666,983 A | 5/1987 | Tsubakimoto et al. |
| 4,734,478 A | 3/1988 | Tsubakimoto et al. |
| RE32,649 E | 4/1988 | Brandt et al. |
| 5,140,076 A | 8/1992 | Hatsuda et al. |
| 5,247,068 A | 9/1993 | Donachy et al. |
| 5,562,646 A | 10/1996 | Goldman et al. |
| 5,599,335 A | 2/1997 | Goldman et al. |
| 5,669,894 A | 9/1997 | Goldman et al. |
| 6,150,469 A | 11/2000 | Harada et al. |
| 6,239,230 B1 | 5/2001 | Eckert et al. |

(Continued)

FOREIGN PATENT DOCUMENTS

EP         0 322 393 A1    6/1989

OTHER PUBLICATIONS

Ahearne et al. "Mechanical Characterization of hydrogels for tissue engineering applications" Topics in tissue engineering 2008; 4 Chapter 12 <http://www.oulu.fi/spareparts/ebook_topics_in_t_e_vol4/abstracts/ahearne.pdf>.*

(Continued)

*Primary Examiner* — Lisa Caputo
*Assistant Examiner* — Jonathan Dunlap
(74) *Attorney, Agent, or Firm* — Andrew A Paul

(57) ABSTRACT

Method for determining the intrinsic gel strength of a water-absorbing hydrogel-forming polymeric material, comprising the step of: obtaining a hydrogel of said water-absorbing polymeric material, submitting said hydrogel to a controlled strain application step and measuring the stress; or submitting said hydrogel to a controlled stress application step and measuring the strain, and determining from said measured stress or strain of step c) the modulus of said hydrogel.

27 Claims, 4 Drawing Sheets

(56) References Cited

U.S. PATENT DOCUMENTS

| | | |
|---|---|---|
| 6,376,618 B1 | 4/2002 | Mitchell et al. |
| 6,391,451 B1 | 5/2002 | Mitchell et al. |
| 2008/0058747 A1* | 3/2008 | Singh Kainth et al. ....... 604/368 |

OTHER PUBLICATIONS

K.S. Anseth, et al., "Mechanical Properties of Hydrogels and Their Experimental Determination", Biomaterials, Elsevier Science Publishers B.V., vol. 17, No. 17, (1996) pp. 1647-1657.

J.A. Stammen, et al., "Mechanical Properties of a Novel PVA Hydroget In Shear and Unconfined Compression", Biomaterials, Elsevier Science Publishers B.V., vol. 22, No. 8, (2001) pp. 799-806.

International Search Report, PCT/US2011/026014, mailed May 10, 2012, 12 pages.

F.L. Buchholz, A.T. Graham: "Modern Superabsorbent Polymer Technology", ACS Wiley & Sons (1998), pp. 6-18, and pp. 167-222.

F.L. Buchholz, N. A. Peppas: "Superabsorbent Polymers: Science and Technology", ACS Symposium Series 573 (1995), pp. 50-76.

P.K. Chatterjee, B.S. Gupta: "Absorbent Technology", Elsevier Science B.V., $1^{st}$ Edition, pp. 285-292 and pp. 310-315.

G. Nisato, F. Schosseler, S.J. Candau: SwellingEquilibrium Properties of Partially Charged Gels: The Effect of Salt on the Shear Modulus, Polymer Gels & Networks, (1996) 4, p. 481-498.

R. Skouri, F. Schosseler, JP Munch, S.J. Candau: "Swelling and Elastic Properties of Polyelectrolyte Gels", Macromolecules, (1995) 28, p. 197-210.

W. Oppermann, S. Rose, G. Rehage: "The Elastic Behaviour of Hydrogels", British Polymer Journal, vol. 17, No. 2 (1985), p. 175-180.

H.M. Wyss, T. Franke, E. Mele, D.A. Weitz: "Capillary Micromechanics: Measuring the Elasticity of Mircoscopic Soft Objects", Soft Matter, (2010) 6, p. 4550-4555.

G. Nisato, R. Skouri, F. Schosseler, J.P. Munch, S. J. Candau: "Elastic Behaviour of Salt-free Polyelectrolyte Gels", Faraday Discuss, (1995) 101, p. 133-146.

F. Schosseler, F. Ilmain, S.J. Candau: "Structure and Properties of Partially Neutralized Poly(acrylic acid) Gels", Macromolecules, (1991) 24, p. 225-234.

F. Horkay, P.J. Bassler, A.M. Hecht, E. Geissler: "Structural Investigations of a Neutralized Polyelectrolyte gel and an Associating Neutral Hydrogel", Polymer, (2005) 46, p. 4242-4247.

C. Sayil, O. Okay: "Macroporous poly(N-isopropyl)acrylaminde networks: formation conditions", Polymer, (2001) 42, p. 7639-7652.

Hrouz, J; Ilaysky, M.; Havlicek, I.; Dusek, K.: Comparison of theViscoelastic Penetration and Tensile Behavior of Poly (Methyl Acrylate) and Poly(Ethyl Acrylate), Collection Czech Chem Comm 44 (1979), p. 1942-1948.

B. D. Johnson, D. J. Beebe, W.C. Crone: "Effects of Seelling on the mechanical properties of a pH-sensitive hydrogel for use in microfluidic devices", Materials Schience & Engineering C, (2004) 24, p. 575-581.

J. Hopfner: "Auswirkung von mechanischen Feldern and Drucken auf gequollene Polyacrylatenetzwerke", 2009 Thesis—Inst. Chem Tech and Polymer Chem—Karlruhe Inst. Tech.

I. Yazicic, O. Okay: "Spatial inhomogeneity in poly(acrylic acid) hydrogels", Polymer, (2005) 46, p. 2595-2602.

O. Okay, W. Oppermann: "Polyacrylamide-Clay Nanocomposite Hydrogels: Rheological and Light Scattering Characterization", Macromolecules, (2007) 40, p. 3378-3387.

K. Haraguchi: "Nanocomposite Gels: New Advanced Functional Soft Materials", Macromol Symp., (2007) 256, p. 120-130.

M. Zhu, Y. Liu, B. Sun, W. Zhang, X. Liu, H. Yu, D. Kuckling, H. P. Adler: "A Novel Highly Resilient Nanocomposite Hydrogel With Low Hysteresis and ultrahigh Elongation", Macromolecular Rapid Communications, (2006) 27, p. 1023-1028.

\* cited by examiner

METHOD FOR DETERMINING THE GEL STRENGTH OF A HYDROGEL

CROSS REFERENCE TO RELATED APPLICATION

This application claims the benefit of U.S. Provisional Application No. 61/308,026, filed Feb. 25, 2010.

FIELD OF THE INVENTION

The present disclosure relates to a method for determining the intrinsic gel strength of a water-absorbing hydrogel-forming polymeric material, by submitting a hydrogel thereof to a controlled shear strain application step and measuring the shear stress or submitting said hydrogel to a controlled stress application step and measuring the shear strain, and determining from said measured stress or strain of step c) the shear modulus (or individual storage and loss moduli) of said hydrogel.

BACKGROUND THE INVENTION

In general, water-absorbent, hydrogel-forming polymeric material (such as material known as absorbent gelling material, AGM, for example formed from polyacrylate polymers), useful in absorbent articles (such as diapers), need to have adequately high sorption capacity in order to perform satisfactory. Furthermore, it may be preferable to also have adequately high gel strength. The sorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles to resist deformation under an applied stress. The gel strength needs to be high enough in the absorbent member or article, so that the particles do not deform and fill the capillary void spaces to an unacceptable degree, causing thereby so-called gel blocking. This gel-blocking inhibits the rate of fluid uptake or the fluid distribution, i.e. once gel-blocking occurs, it can substantially impede the distribution of fluids to relatively dry zones or regions in the absorbent article and leakage from the absorbent article can take place well before the water-absorbent polymer particles are fully saturated or before the fluid can diffuse or wick past the "blocking" particles into the rest of the absorbent article.

When developing new water-absorbent polymeric materials or absorbent articles therewith, manufacturers of such materials or articles measure thereto frequently measure the capacity and gel strength of such newly developed materials.

The gel strength of such particulate materials is for example determined by swelling these particles in saline solution and determining the Saline Flow Conductivity test method, well know in the art, and for example described in U.S. Pat. No. 5,599,335, U.S. Pat. No. 5,562,646 and U.S. Pat. No. 5,669,894.

The inventors found however that during development of new water-absorbent hydrogel-forming polymeric materials it would be useful to be able to measure the gel strength of such hydrogels. The inventors also found that it is desirable to be able to test the gel strength of the material directly after production, of for example the base polymer, and for example before further surface cross-linking and/or before drying or particle formation steps. The inventors found that this can help in determining the impact of specific chemistry of the base polymer or specific properties of the base polymer on the intrinsic gel strength, without the influence of drying steps, particle formation steps etc. Furthermore, there is a need to determine the intrinsic gel strength with a method that reflects better the in-use situation, e.g. when a wearer wears an absorbent article (such as an infant wearing a loaded diaper (full or urine) and moving with the diaper, sitting on the diaper etc.). Furthermore, the inventors found that there is a need for a test method that can measure the intrinsic gel strength on hydrogels of the water-absorbent polymeric material, comprising high levels if fluid (e.g. reflecting a real-use situation of a (fully) loaded diaper).

SUMMARY OF THE INVENTION

The present disclosure relates to a method for determining the intrinsic gel strength of a (e.g. water-absorbing) hydrogel-forming polymeric material, comprising the step of:
a) obtaining a hydrogel of said (water-absorbing) hydrogel-forming polymeric material (for example comprising polyacrylate polymers), comprising at least 5 g/g or at least 10 g/g or at least 50 g/g, at least 100 g/g, or even at least 150 g/g of an aqueous liquid;
b) optionally shaping said hydrogel of step a) in the form of a test sample hydrogel;
c) submitting said hydrogel of step a) or of said optional step b) to a controlled shear strain application step and measuring the shear stress; or
submitting said hydrogel of step a) or of said optional step b) to a controlled shear stress application step and measuring the shear strain,
d) determining from said measured stress or strain of step c) the shear modulus of said hydrogel.

In one embodiment, said method step c) involves the use of a rheometer, applying a controlled oscillating shear strain or controlled oscillating shear stress (e.g. torque/volume). Hereby, the oscillation rate and/or frequency can for example be controlled.

The disclosure also relates to a method for determining the intrinsic gel strength of a (e.g. water-absorbent) hydrogel-forming polymeric material, comprising the step of:
a) obtaining a hydrogel of said (e.g. water-absorbent) hydrogel-forming polymeric material (for example comprising polyacrylate polymers), comprising at least 5 g/g or at least 10 g/g or at least 50 g/g, at least 100 g/g, or even at least 150 g/g of an aqueous liquid;
b) optionally shaping said hydrogel of step a) in the form of a test sample hydrogel;
c) applying a controlled uniaxial displacement compression strain to said hydrogel of step a) or of optional step b), (optionally while allowing substantial maintenance of the volume of said hydrogel and/or ensuring the substantial absence of confining pressure); and measuring the stress (e.g. to upheld the compression displacement) of said hydrogel; or
applying a controlled uniaxial compression stress to said hydrogel of step a) or of optional step b), (optionally while allowing substantial maintenance of the volume of said hydrogel and/or ensuring the substantial absence of confining pressure); and measuring the strain of said hydrogel;
d) determining from said measured stress of step d) the Young compression modulus of said hydrogel.

It is apparent that the test methods herein determine the intrinsic gel strength of a hydrogel (sample), independent of properties such as particle properties such as size, morphology, shape, surface area.

One of the benefits of this test method is that it can be performed on a hydrogel formed from an aqueous liquid and a (water-absorbent) hydrogel-forming polymeric material, e.g. with any suitable liquid uptake level (test capacity), for example directly after production of said polymeric material, but for example prior to subsequent process steps, such a surface treatment, drying, particle formation (e.g. grinding, sieving).

Said water-absorbent hydrogel-forming polymeric material herein may be swollen to its equilibrium state in said liquid to form said hydrogel of step a), ("equilibrium hydrogel"), optionally by allowing said polymeric material to swell in said liquid for at least 72 hours, preferably at least 1 week.

Typically, the hydrogel sample is placed on a horizontal test surface, e.g. without the need of clamping. This is advantageous, in particular for hydrogels comprising larger amounts of aqueous liquid, e.g. more than 5 g/g, or more than 10 g/g. In one embodiment herein, the step c) is done on a hydrogel that is in contact, e.g. immersed in an aqueous liquid during step c).

The test methods herein may also be used for hydrogels formed from an aqueous liquid and a polymeric material that has been submitted to additional processing steps such as a surface treatment step, drying step, particle formation step, including grinding step, or combinations thereof. The methods may be used to determine the impact of for example such an additional process step (e.g. drying) on the intrinsic gel strength of said polymeric material, by determining the intrinsic gel strength of a hydrogel of said polymeric material not submitted to such an additional process step and the intrinsic gel strength of a hydrogel of said polymeric material that has been submitted to such an additional process step, and comparing the obtained intrinsic gel strength values.

The methods herein may comprise the step of determining the liquid content of said hydrogel ("test capacity") to be tested or that is tested, either prior or during step a) or b), or subsequent to step c) or d), to determine the intrinsic gel strength of said water-absorbent hydrogel-forming polymeric material at said "test capacity". The method may be repeated with hydrogel(s) with the same polymeric material but with different test capacities, e.g. the difference being for example at least 30%, in order to obtain the intrinsic gel strength-capacity trade-off relationship.

The methods herein may also be repeated for different hydrogel-forming polymeric materials, the difference being for example a different level of internal cross-linking or surface cross-linking, e.g. this being for example at least a 30% increase or decrease of the level of surface crosslinker agent present (e.g. in the hydrogel), as described herein.

The intrinsic gel strength can be used as an input parameter for computer models, e.g. from which (water-absorbent) hydrogel-forming polymeric material properties related to the intrinsic gel strength can be predicted.

DETAILED DESCRIPTION OF THE INVENTION

Figure 1:
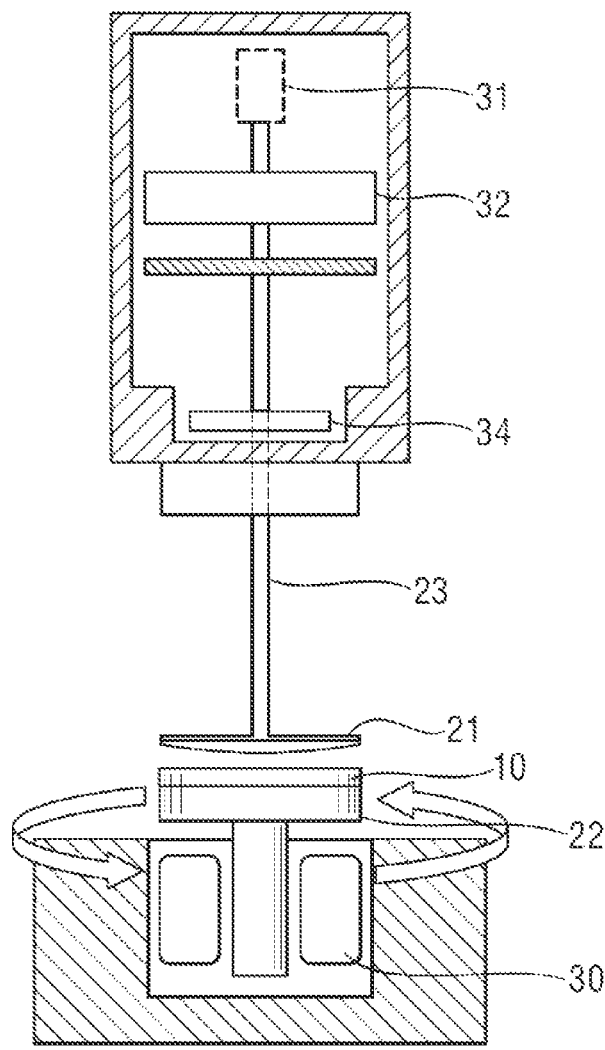
FIG. 1 is a schematic view of a controlled shear strain-applying test equipment.

A method disclosed herein is for measuring the intrinsic gel strength of a hydrogel, formed from an aqueous liquid and a hydrogel-forming polymeric material.

The intrinsic gel strength can be understood to be the total resistance of the gel to deformation, comprising the (predominantly) elastic (reversible) and the viscous (irreversible) contributions (e.g. describing a coherent material which can be thought of as having "infinite" size).

The intrinsic gel strength herein is for example derived from the shear modulus or Youngs compression modulus, e.g. without contributions from gel morphological or volume changes.

The polymeric material herein is referred to as hydrogel-forming, which means that it forms a gel upon contact with, and (ab)sorption of, an aqueous liquid, including for example water or an aqueous solution and/or dispersion, i.e. to form thus a hydrogel (as known in the art); it should be understood that the polymeric material may be able to form a gel upon contact with other liquids too.

In one embodiment, the aqueous liquid herein may for example be urine, blood, or for example a saline solution, for example a 0.9% saline solution (NaCl in demineralised water), as further described herein.

The polymeric material herein is referred to as a water-absorbent polymeric material, which means that it is capable to absorb (at least) aqueous liquids as described herein, such as water and/or an aqueous solution and/or dispersion, such as urine, blood, or for example a saline solution, as above. Obviously, the polymeric material may absorb other liquids too.

The polymeric material herein may be any water-absorbent hydrogel-forming polymeric material (e.g. comprising or consisting of water-absorbent hydrogel forming polymers). Examples include polymers that are typically (lightly) crosslinked polymers, optionally lightly crosslinked hydrophilic polymers. While these polymers may in general be non-ionic, cationic, zwitterionic, or anionic, the polymers may be cationic or anionic. Acid polymers may be used, which contain a multiplicity of acid functional groups such as carboxylic acid groups, or their salts, which may be sodium salts. Examples of acid polymers suitable for use herein include those which are prepared from polymerizable, acid-containing monomers, or monomers containing functional groups which can be converted to acid groups after polymerization. Such monomers include olefinically unsaturated carboxylic acids and anhydrides, and mixtures thereof. The acid polymers can also comprise polymers that are not prepared from olefinically unsaturated monomers. Examples of such polymers also include polysaccharide-based polymers such as carboxymethyl starch and carboxymethyl cellulose, and poly(amino acid) based polymers such as poly(aspartic acid). For a description of poly(amino acid) absorbent polymers, see, for example, U.S. Pat. No. 5,247,068, issued Sep. 21, 1993 to Donachy et al. Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid and anhydride monomers useful herein include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride. Water-absorbent hydrogel forming polymers contain carboxyl groups may be utilized, such as the above-described carboxylic acid/carboxylate containing groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the aforementioned copolymers, polyacrylic acid, and slightly network crosslinked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478. Some polymer materials used for making the water-absorbent polymers herein are polyacrylates/acrylic acids and derivatives thereof, (slightly) network crosslinked polymers partially neutralized polyacrylic acids and/or—starch derivatives thereof. It may be that partially neutralized polymeric acrylic acid is used herein. In some instances, the water-absorbent polymers comprise from about 50% to 95% (mol percentage), about 75 mol % neutralized, polyacrylic acid (i.e., poly (sodium acrylate/acrylic acid)), optionally crosslinked e.g. with a crosslinking agent level of between 0.005 to 2.0 mol % (based on monomer level). The water-absorbent polymers can be formed by any polymerization and/or crosslinking techniques. Typical processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986; U.S. Pat. No. 5,140,076 (Harada); U.S. Pat. No. 6,376, 618 B1, U.S. Pat. No. 6,391,451 and U.S. Pat. No. 6,239,230 (Mitchell); U.S. Pat. No. 6,150,469 (Harada). Crosslinking can be affected during polymerization by incorporation of suitable crosslinking monomers. Alternatively, the polymers can be crosslinked after polymerization by reaction with a suitable reactive crosslinking agent.

The polymeric material herein may be in a solid state comprising substantially no water. Then, in step a) a hydrogel is formed from this polymeric material. This can be done by any known method. In one embodiment, the polymeric material, e.g. in solid state, is contacted by the aqueous liquid, for example by submerging the polymeric material in said liquid. This may be done with a pre-determined amount of liquid, in a manner that ensures accurate absorption of said liquid, so the hydrogel has a predetermined liquid intake (test capacity); alternatively, and in one embodiment, this can be done with an excess amount of liquid (for example at least 5× the expected absorbent capacity of the polymeric material, or at least 10× said capacity), where after the polymeric material may absorb only a certain amount of the excess liquid, and said amount (test capacity) can be determined subsequently, prior to or after testing step c).

In one embodiment, the polymeric material is brought in contact with the aqueous liquid in an excess amount, e.g. submerged, and allowed to form an "equilibrium hydrogel", e.g. a hydrogel of the polymeric material that has (ab)sorbed its equilibrium amount of said aqueous liquid. This may be done by contacting, e.g. submerging, the polymeric material in an excess amount of aqueous liquid for at least 24 hours, at least 48 hours, or at least 72 hours, or for example at least 1 week, or for example at least 2 weeks. Equilibrium swelling may take even three weeks or more. During the formation of the hydrogel, in particular when done over prolonged period of time, e.g. of more than 24 hours, the aqueous liquid is exchanged, as known in the art. During hydrogel formation, the liquid and polymeric material and hydrogel being formed is covered and kept in controlled conditions.

Typically, this is done at predetermined ambient conditions, such as 20° C. Gentle movement of the solution by uses of an orbital shaker can help formation of a homogenous hydrogel (e.g. equal swelling). If required, the degree of swelling, and hence the amount of (ab)sorbed liquid by the polymeric material and present in the hydrogel, can be monitored by periodic weighing of the hydrogel.

In another embodiment, a polymeric material may already comprise an aqueous liquid, and optionally already be in the form of a hydrogel of said polymeric material, but it is contacted with, and allowed to absorb additional aqueous liquid, to obtain the hydrogel to be tested in the method disclosed herein.

In an additional or another embodiment herein, the polymeric material is obtained by a polymerization process involving the use of an aqueous liquid, and the resulting hydrogel of the resulting polymeric material may then comprise at least part of said aqueous liquid; this hydrogel may then be submitted to the test method, or this hydrogel may be a "precursor hydrogel" that is further allowed to absorb an aqueous liquid, as set out above, and then tested in the method. For example, the polymeric material may be obtained by a process of polymerising polymerizable units (e.g. monomers) in the presence of an aqueous liquid and optionally further compounds, (e.g. for example an aqueous solution or dispersion of said polymerizable units (e.g. monomers), and optionally cross-linking agent(s)), and the resulting hydrogel may thus comprise said aqueous liquid. Alternatively, or in addition, the polymeric material may be polymeric material that has been submitted to an additional process step after polymerisation, herein referred to as post-treated polymeric material, and said additional process step involved an aqueous liquid. For example, the additional process step may be a surface cross-linking step, or a coating step with an aqueous dispersion or solution of a coating agent.

In one embodiment, the hydrogel to be submitted to step c) is obtained by allow (absorption and hence hydrogel forming of a polymeric material or pre-cursor hydrogel in demineralised water, or in a aqueous saline solution, typically between 10 and 0.05% wt/vole saline solution (in demineralised water).

In order to obtain test results that reflect well the intrinsic gel strength of polymeric material and its hydrogels in use in a urine absorbing article, e.g. a diaper, the aqueous liquid is typically 0.9% NaCl wt/vol solution (herein referred to as 0.9% saline).

The hydrogel can be directly obtained in the right size and shape to be tested in the test method. For example, the hydrogel can be obtained by forming the polymeric material from polymerizable units in the presence of the aqueous liquid in a vessel that has the size dimension(s) suitable for the test method herein, for example into a substantially flat plate shape (with limited Z-dimension, as described below), suitable for submitting to step c).

In another alternative or additional embodiment, a hydrogel is obtained, as described herein, and submitted to the optional step of shaping the hydrogel into a hydrogel sample (herein referred to as optional step b); such a hydrogel sample is, for easy of description, herein referred to as "hydrogel". The shaping of a hydrogel into a suitable hydrogel for testing, e.g. a hydrogel sample of the desired dimensions as for example described herein below, can be done by any known method, such as cutting with a punch die.

The dimensions are typically chosen such that the measured moduli are still in the linear visco-elastic region and that substantially no shape deformation occurs along the sides of the hydrogel that is tested.

In one embodiment herein, the hydrogel to be tested in step c) (sample) has a thickness direction Z, which is less than the width and/or length dimension and/or diameter (X, and/or (X,Y) dimension) of said hydrogel, e.g. the ratio of the Z-dimension to the X-dimension and/or to the Y-dimension or the diameter is for example from 1:2 to for example 1:50, or from 1:3 to 1:30. In one embodiment, the width and/or length, or diameter dimension of the hydrogel in step c) is from 1.0 cm to 20 cm, up to 15 cm or to 10 cm, or any size required by the test equipment used herein.

The thickness is for example from 0.5 to 10 mm; or from 1.0 mm to 5 mm; for the shear modulus method herein, the thickness may for example be up to 3 mm or up to 2 mm; for the Young compression modulus method herein, the thickness may for example be up to 6 mm or up to 5 mm. The hydrogel, or the part thereof that is submitted to the test method, and may have a homogeneous thickness.

The thickness of the hydrogel can be measure with a micrometer gauge, or it is measured by the test equipment used herein to do the method herein, e.g. rheometers useful herein measure the thickness of the hydrogel sample. For the shear modulus measurements using a rheometer, as described herein below, the hydrogel to be tested typically requires a circular "plate shape" with a 40 mm diameter (X dimension) or a 25 mm diameter or 10 mm. For the Young modulus method described herein below, the hydrogel may have a diameter of for example 13 mm.

The hydrogel may be such that the opposing surfaces in the X-Y plane parallel, and may be flat.

Once the hydrogel is obtained, it is submitted to step c) of the test method, involving the application of a controlled stress or a controlled strain, herein referred to as applied stress or applied strain, for simplicity. Obviously, the hydrogel may also be submitted to both a controlled strain applications step or a controlled stress application step, in consecutive manner, in any order.

"Controlled" as used herein means that the application of the amount of stress or strain is controlled, e.g. such that the amount of stress or strain to be applied can be predetermined and set to a certain value, and can be altered during the measurement or for subsequent measurement (e.g. on the same hydrogel (sample)).

For example, the amount of strain applied or the amount of stress applied is controlled such that a predetermined (set) stress or strain is applied, to measure the resulting strain or stress, respectively, of the hydrogel at that set applied stress or strain, respectively. The applied stress or strain can then be altered and set to a different value (controlled), and further resulting strain or stress measurement, respectively, can be obtained.

The strain applied or measured is typically a displacement applied to the sample. The stress that is applied or measured has as unit of (force/area); in one embodiment, the stress may be a measured as torque/volume (torque is force×distance).

In one embodiment, the applied stress or strain is a uniaxial applied compression stress or uniaxial applied displacement (compression) strain, to measure the Young compression Modulus E, or the Young compression storage modulus E' and the Young compression loss modulus E". In another embodiment, the applied stress is a shear stress or the applied strain is a shear strain, and the measured modulus is the shear modulus G, or the storage shear modulus G' and the loss shear modulus G". For example, the shear strain or shear stress applied may be an oscillation shear strain or an oscillation shear stress, controlled to have a predetermined (set) oscillation amplitude and/or frequency. After a measurement, this may then be subsequently set (controlled) to an altered applied stress or strain.

The method herein, applying a controlled shear strain or a controlled shear stress in step c), may be controlled by:— oscillating time sweep, in which said hydrogel is measured under fixed frequency and amplitude, for a length of time. (E.g. this may determine if there are any time effects to perturbing the hydrogel). Hereby, in one embodiment herein, it may be that a controlled strain is applied in step c);— oscillating amplitude sweep (ramp), in which the frequency is fixed and the amplitude is varied, e.g. over a pre-determined range (ramp). From this experiment, suitable % strain (or stress) amplitudes can be determined for the oscillatory time sweep experiment.

Frequency sweep (ramp) in which said hydrogel is measured under a fixed amplitude and the frequency is varied, e.g. over a pre-determined range (ramp). From this experiment, suitable frequencies can be determined for the time sweep experiment.

Figure 2:
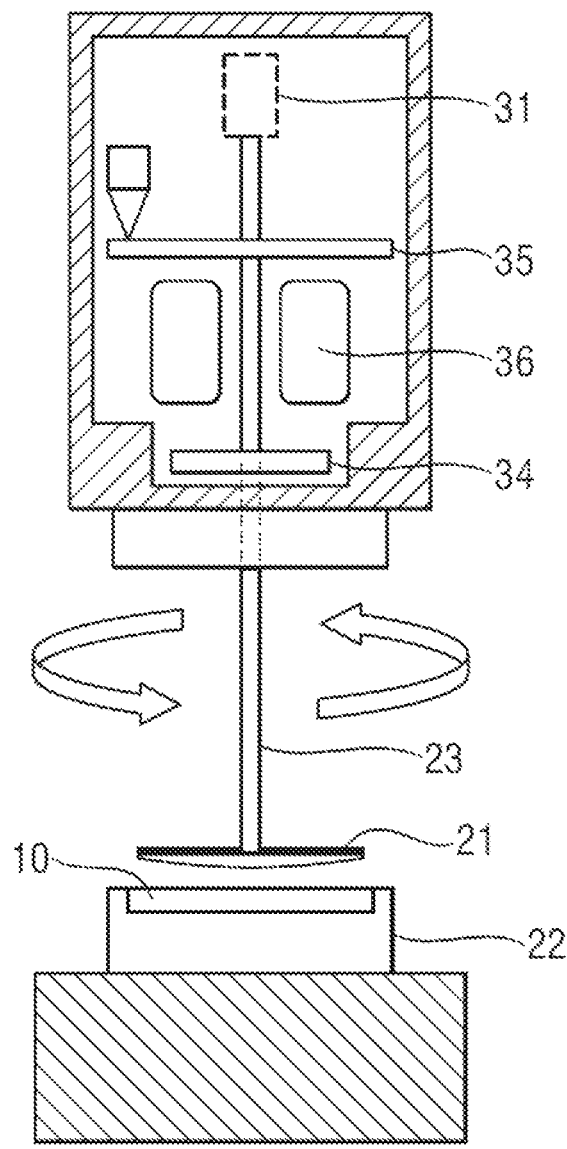
FIG. 2 is a schematic view of a controlled shear stress-applying test equipment.
Figure 3:
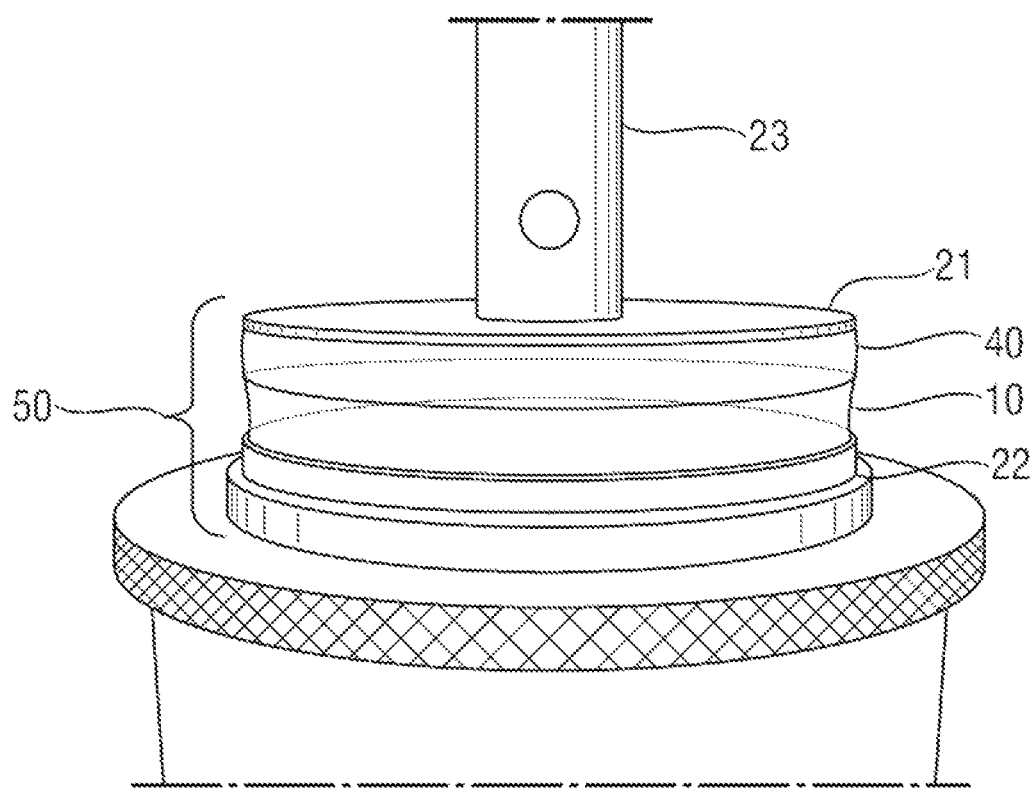
FIG. 3 is a cross-sectional view of a hydrogel as introduced between opposing first and second test surfaces, with aqueous liquid.

In one embodiment herein, step c) comprises the step of applying a controlled stress or strain onto a horizontally placed hydrogel sample, placed onto a first horizontal test surface (having thus a thickness dimension Z that is vertical and thus perpendicular to the test surface), as for example shown in FIGS. 1, 2 and 3.

In FIG. 1, a schematic view of controlled shear strain-applying test equipment suitable for use with the invention is shown. It comprises a normal force transducer 31, a stress (torque) measurement tool 32, a frictionless rotation tool and bearing 34, a vertical connection 23, a second test surface 21, a first test surface 22, and a strain applying motor(s) 30. Also shown in the figure, is a hydrogel 10.

In FIG. 2, a schematic view of controlled shear stress-applying test equipment suitable for use with the invention is shown. It comprises a normal force transducer 31, a strain (displacement) measurement tool 35, a stress (torque) applying motor(s) 36, a frictionless rotation tool and bearing 34, a vertical connection 23, a second test surface 21, and a first test surface 22. Also shown in the figure, is a hydrogel 10.

In FIG. 3, a cross-sectional view of a hydrogel as introduced between opposing first and second test surfaces, with aqueous liquid, and suitable for use with the invention is shown. It comprises a vertical connection 23, a second test surface 21, a liquid 40, and a first test surface 22. Also shown in the figure, is a hydrogel 10.

A controlled strain, for example a shear strain (as shown for example in FIG. 1) may be applied to the sample by applying a rotating displacement, and for example with a oscillating varying force with fixed amplitude and/or frequency, to the hydrogel, for example by rotating said test surface by one or more stepper motors.

The resulting stress (e.g. torque/volume) may be measured by any means, for example by use of a torque rebalance transducer and a knowledge of the sample volume, which can be calculated from the Z and X or X and Y dimensions of the sample, and which is typically calculated in the instrument vendors software from the gap distance and area of the plate used.

An alternative method herein comprises the step c) of applying a controlled stress, e.g. torque/volume, to a hydrogel. The stress applied may for example be applied onto said hydrogel with a motor (typically frictionless) via one of said test surfaces, for example in an oscillating manner with controlled (set) amplitude and/or frequency. The strain may be measured with for example an optical encoder that can measure precisely the displacement of the hydrogel, as known in the art.

In some methods herein, the hydrogel is placed horizontally on a first test surface to support the hydrogel sample. A further component of the test apparatus may be a second test surface that is then placed in direct or indirect contact with the top surface of the hydrogel; either of the test surfaces may transfer the stress or strain to the hydrogel sample; the test surfaces may be plates with a horizontal flat surface, a may be a circular shape, but it may have a different geometric shapes.

The test surface or test surfaces herein may be roughened, e.g. they may be roughened plates; they may for example have grooves.

In an embodiment herein, step c) may comprise the step of placing at least one surface of the hydrogel (e.g. surface opposite to test surface, as for example shown in FIG. 1) in complete contact with an aqueous liquid, optionally the same liquid as used in step a) and/or absorbed by the water-absorbing polymer to form the hydrogel. The hydrogel may be immersed in said aqueous liquid in step c). This may for example be done by placing the hydrogel in a test vessel with said liquid, which allows the application of stress or strain on the surface of said hydrogel.

In order to measure the stress or strain accurately, the measurement is done with minimal friction (within the equipment), and/or under controlled temperature and humidity conditions for the hydrogel, for example 20° C. and 80% RH. Temperature control may for example be done with a Pelletier device.

A suitable tool herein is a strain controlled rheometer, such as for example available from TA Instruments, model ARES or ARES G2. A further suitable tool is a controlled stress application rheometer, as for example available from TA Instruments, model AR2000 or ThermoSciences' HAAKE RheoStress I. Other suitable equipment for both stress controlled or strain controlled methods includes Malvern's Kinexus, Bohlin's Gemini, Anton Paar MCR, ATS Rheosystem's Nova.

In the shear modulus-measurement method herein, a slight compression force (i.e., normal force) may be applied to the hydrogel, e.g. to the test surface(s), to make sure the hydrogel is immobilised, e.g. gripped by the test surface(s). This is typically less than 0.1 Pa. The equipment may thereto comprise a Normal force transducer.

In one embodiment, the method is to determine the intrinsic gel strength by measuring the Youngs compression modulus, by applying a controlled (compression displacement) strain or stress on a hydrogel (as described above), while typically allowing substantial maintenance of the volume of said hydrogel and/or ensuring the substantial absence of confining pressure and measuring the counter pressure of said hydrogel, and then determining the Young compression modulus of said hydrogel. The hydrogel preparation, and test conditions as setout apply equally to this alternative method. For example, a DMA instrument, with parallel compression plates, can be suitably used herein, e.g. a TA Instruments model Q800.

In one embodiment herein, the sample is placed on the test surface and allowed to condition and rest prior to test step c), for example for at least 30 minutes, or at least 1 hour, while immersed in said aqueous liquid, as described above, to avoid drying out.

FIG. 3 shows an embodiment, wherein in step c) the hydrogel is placed onto a first horizontal test surface and contacted with said aqueous liquid (being immersed in it) and contacted with a second test surface; hereby both test surfaces may be for example plates with horizontal flat surfaces, in contact with either the hydrogel and/or the liquid. The liquid may for example cover the upper second test surface (but not exceeding it). (FIG. 3 does not show the vessel that contains (and serves to retain) the aqueous liquid.)

In an embodiment herein, step c) is done in a controlled manner such that the stress-strain relationship remains within the linear visco-elastic (LVE) region; then, the equation is:

$$\sigma = G\gamma$$

Stress=modulus×Strain; for example, the shear strain, and for example the set frequency, is then thus controlled such that this relationship applies.

The viscoelastic region of a hydrogel can be determined for example by applying a certain force onto the hydrogel, for example between 0.1N or 0.15N and 0.3N, or for example 0.2N. A measurement can then be done to determine when the storage and loss moduli (shear storage modulus G' and shear loss modulus G"; or Young storage modulus E' and Young loss modulus E") begin to increase, so where the operating boundary is. For example, for the rheometer test herein, a frequency sweep oscillatory measurement is performed over a range, for example 0.1-5 rad/s, to determine where the storage and loss moduli (G' and G") begin to increase. Then, a frequency contained within the flat portion of the curve (LVE region) is selected for the method herein (for example a value between 0.1 and 1 rad/s). An amplitude sweep is then done, at a selected frequency from the step above, to determine suitable amplitudes (for example, from a % strain of 0.01 to 1, or stress from 0.01 Pa to 10 Pa). Amplitudes are likewise selected from the LVE region.

Typically, a storage modulus G' or E' and a loss modulus G" or E" are obtained with the method, and the shear modulus is in fact a combination of G' and G" or E' and E" (e.g. G=square root $(G'^2+G''^2)$.

In one embodiment herein, G'>>G" and the shear modulus G of step d) is substantially equal to the storage modulus G'. The shear storage modulus is then a measure of the intrinsic gel strength of the hydrogel tested. In another embodiment herein, E'>>E" and the shear modulus G of step d) is substantially equal to the storage modulus G'. The Young storage modulus is then a measure of the intrinsic gel strength of the hydrogel tested. (>> being a fraction of at least 5×, or at least 10×, or at least 15× or at least 20×).

For example, a horizontally placed sample, placed on a horizontal test surface is covered with a horizontal compression clamp for example until a force reading of 0.01N. Then, for example a strain rate ramp is run, typically from 1%/min to 5%/min. The stress is then measured and the compression Modulus can be determined (e.g. as the slope of the stress/strain gradient within the linear visco-elastic linear region).

The methods herein may comprise the step of determining the liquid content of said hydrogel ("test capacity") to be tested or that is tested, either prior or during step a) or b), or subsequent to step c) or d), for example to determine the intrinsic gel strength of said water-absorbent hydrogel-forming polymeric material at said "test capacity". This may be done by determining the test capacity of part of the hydrogel and submitted another part to the method step c) herein, and assuming homogeneous uptake of the liquid and hence a homogenous capacity of the hydrogel. It may alternatively, or in addition be determined after the step d) on the tested hydrogel. Determination of the amount of liquid in the hydrogel (test capacity) may be done by any known method; for example, the hydrogel may be weighed, and then dried to obtain the dry polymeric material, and measuring the dry weight thereof. The weight loss corresponds to the test capacity. If the aqueous liquid of the hydrogel is a saline solution, a further step may be used to remove the NaCl, i.e. an extraction step as known in the art (for example with ethanol/water), to obtain a dry polymeric material, free of NaCl, and weighing this polymeric material as well.

This method herein may be repeated with hydrogels comprising the same polymeric material but with different test capacities, e.g. the difference being for example at least 30 g/g, or at least 50 g/g, or at least 100 g/g. This may provide an indication of the influence of the absorption on the intrinsic gel strength.

In one embodiment, the method is repeated on a multitude of hydrogels, for example at least 2, or at least 3, or at least 4, that each have a different chemistry, for example each having a different level of cross-linking, or a different level of surface crosslinking, or a different coating agent, or a different level of coating agent, or the polymers being made from different polymerizable monomers, and/or other chemical properties known to influence the (intrinsic) gel strength of a polymeric material. Then, each hydrogel may comprise the same test liquid and may have the same test capacity (uptake), so that a variation in the modulus and intrinsic gel strength can be directly related to the difference in chemistry of one hydrogel to another.

For example, different hydrogels may be tested, the difference being for example a different level of internal cross-linking or surface cross-linking, e.g. this being for example at least a 30% or for example at least 50% or at least 100% increase or decrease of the level of crosslinking agent present (e.g. in the hydrogel) (mol % per monomer level). For example, the (e.g. internal or surface) crosslinking agent may be present at a level (mol % per monomer level) of between 0.01 mol % to 5 mol % for all hydrogels tested, but each hydrogel has a different level, the difference being at least 30%.

For example, a first hydrogel may comprise for example 0.05 mol % crosslinking agent, and/or a further hydrogel may comprise for example 0.1 mol % crosslinking agent, and/or a further hydrogel may comprise for example 0.3 mol % crosslinking agent, and/or a further hydrogel may comprise for example 1.0 mol % crosslinking agent. This is for example exemplified in FIG. 4 and the example below.

The methods herein may in addition or alternatively be repeated for different hydrogel-forming polymeric materials, the difference being for example the presence of different monomers used to form the polymeric material; or different levels thereof, said difference being at least a 30% increase between different hydrogels; for example, a first hydrogel comprises polymeric material formed from a single type of monomers, a further hydrogel is formed from a polymeric material formed from two or more monomers that are different to one another (whereof the ratio of a first to a second monomer is at least 1:1000, for example).

In any of the embodiments above, the different hydrogel can be tested with any of the methods herein, and the obtained intrinsic gel strength values of the different hydrogels can be compared, to understand the influence of said differences on the intrinsic gel strength and hence the performance of the polymeric material in use.

EXAMPLE

Procedure for the preparation of a hydrogel or precursor hydrogel disk of polyacrylate polymer and aqueous liquid To 200 g of glacial acrylic acid (AA) (Merck) an appropriate amount of the core crosslinker (in the amounts indicated below) MethyleneBisAcrylAmide, MBAA, from Aldrich Chemicals) is added and allowed to dissolve in said acrylic acid at ambient temperature. An amount of water is calculated (633 g) so that the total weight of all ingredients for the polymerization equals 1000 g (i.e. the concentration of AA is 20 w/w-%). 150 mg of the initiator potassium peroxodisulfate ($K_2S_2O_8$) (Merck) is dissolved in approx. 20 ml of this deionized water. 166.5 g of 50% NaOH is weighted out separately in a Teflon or plastic beaker.

Approx. half of the calculated amount of water is added as crushed ice (made from deionized water) into a 2l Erlenmeyer flask, and a large magnetic stirrer is added. Next, the 50% NaOH is added to the ice, and the resulting slurry is stirred. Then, while stirring is continued, the acrylic acid/MBAA is added within 10 minutes (if the temperature rises above 50° C., then a slower addition e.g. 15 min. is used), followed by the remaining water. The resulting solution is clear, all ice melted, and the resulting temperature is typically 15-25° C. At this point, the initiator solution is added. Finally, 400 mg of hydroxyl-2-methyl propiophenone (Merck) is added via a plastic pipette while stirring is continued.

This solution is then transferred into a glove box in which an oxygen depleted argon atmosphere is maintained at <50 PPM oxygen. 30 ml portions of the batch as described above are poured (with an Eppendorf pipette) into flat, 10 cm diameter Teflon dishes and let equilibrate in the glove box atmosphere for 3 minutes. Thereafter, polymerization is initiated via irradiating the dishes for 90 seconds via a 366 nm UV lamp (CAMAG). (To ensure a constant UV light yield, the UV lamp is preheated for approximately 60 mins before using it.) The distance lamp—dish is approx. 12 cm. Polymerization of the self-heating disks is allowed to proceed in the glove box.

The resulting hydrogels or precursor hydrogels are allowed to equilibrate at RT, as described herein, for one day before submitted it to the test herein, or, in the event a precursor hydrogel is obtained, to further absorption of aqueous liquid (to form the hydrogel to be tested).

This is repeated with different amounts of MBAA, to obtain different hydrogels:
Hydrogel 1: (1.0 mole % MBAA)
Hydrogel 2: (0.1 mole % MBAA)
Hydrogel 3: (0.03 mole % MBAA)

Example 2

Hydrogel 4

The example 1 above is repeated as above, with however a different initiator system, namely TEMED/$K_2S_2O_8$, at 60° C. (for example 0.124% TEMED and 0.2% $K_2S_2O_8$ w/w-% of AA, added instead of the initiators stated above). Furthermore, for this experiment, the 30 ml solution again is poured into flat 10 cm Teflon dishes and these are then placed into a sealable plastic container; this container itself is then placed into two Ziploc-bags and sealed (all in the oxygen depleted atmosphere of a glove box). Then, this assembly is brought into a circulation oven preheated to 60° C. and left there for polymerization for 12 hours. The assembly is removed from the box, and the resulting hydrogels or precursor hydrogels are allowed to equilibrate at RT, as described herein, for one day before submitted it to the test herein, or, in the event a precursor hydrogel is obtained, to further absorption of aqueous liquid (to form the hydrogel to be tested).

Shear Strain Application and Measurement

Several Hydrogel samples 1-3 were separately allowed to swell to equilibrium state in 09% saline for 3 weeks.

Figure 4A:
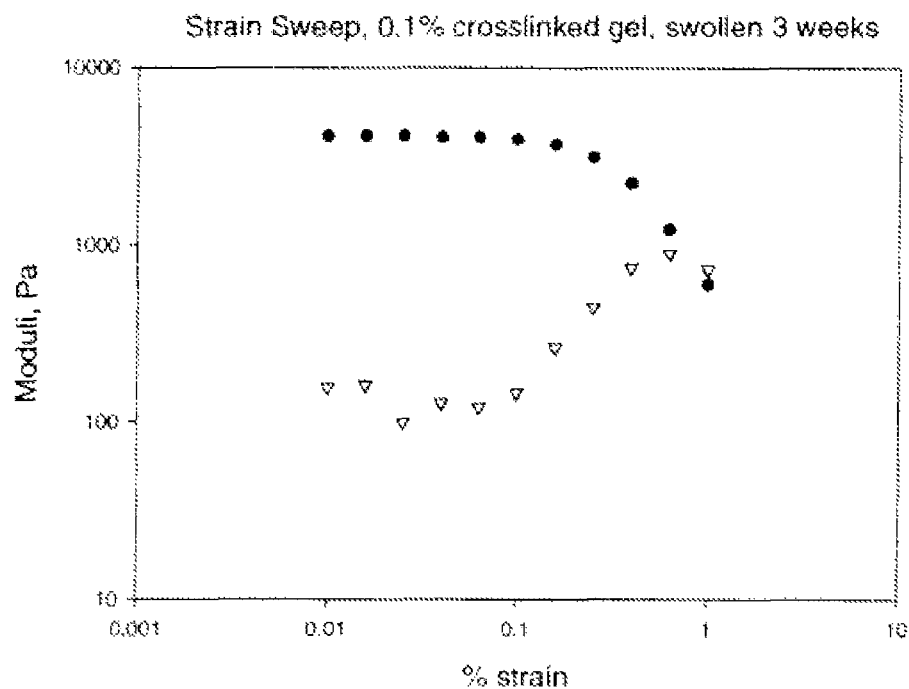
FIG. 4A is an exemplary strain sweep curve showing the storage modulus G'>>loss modulus G".

The thus obtained equilibrium hydrogel 2 was submitted to the shear strain application method by use of a controlled strain application rheometer, available from TA Instruments, model ARES. FIG. 4A shows the strain sweep curves for the Shear Storage Modulus G' and the Shear Loss Modulus G". This shows that the Shear Modulus can be taken to substantially equal the Shear Storage Modulus G' and hence intrinsic gel strength, changes when the applied strain is changed on equilibrium Hydrogel 2.

Further hydrogel samples 1-3 where allowed to swell to the following, different test capacities:

| Sample Number | Capacity, g uptake/g solids | Storage Modulus, G' (Pa) |
|---|---|---|
| Hydrogel 1 | 16.81 | 4172.6 |
| Hydrogel 2 | 48.24 | 319.5 |
| Hydrogel 3 | 73.34 | 69.0 |
| Hydrogel 3 | 197.0 | 25.3 |

Figure 4B:
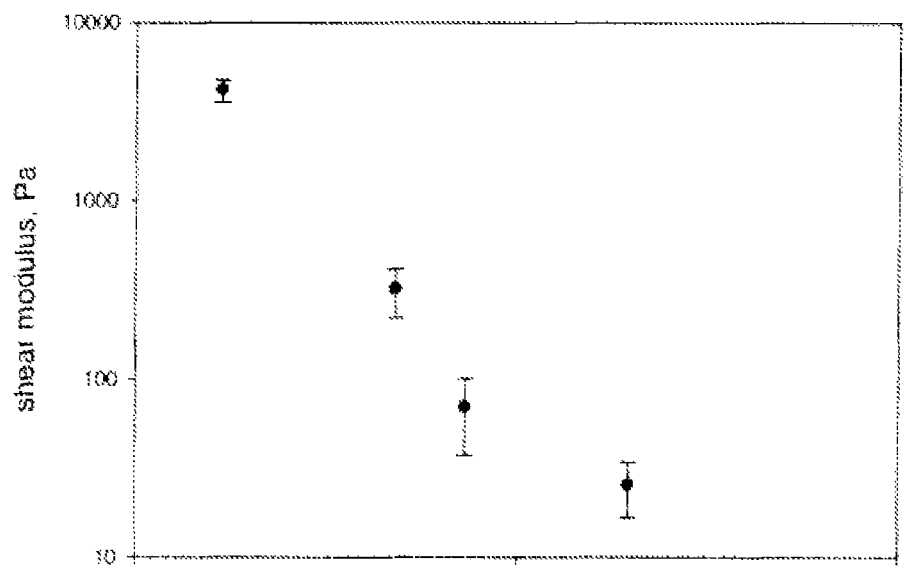
FIG. 4B is an exemplary curve, showing the variation in Shear Moduli for hydrogels with different internal crosslinking levels, at certain test capacities, and the impact of the increase of test capacity on the intrinsic gel strength of hydrogels comprising the same polymeric material

FIG. 4B shows the difference in shear modulus (shear storage modulus), and hence intrinsic gel strength, between hydrogels samples 1, 2, and 3 and hydrogels 3 (with different test capacity) at test capacity set out above. It also shows for hydrogel 3 the impact on the intrinsic gel strength by the increase in test capacity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining the intrinsic gel strength of a water-absorbing hydrogel-forming polymeric material, comprising the steps of:
    a) obtaining a hydrogel of the water-absorbing polymeric material, comprising at least about 5 g/g, of an aqueous liquid;
    b) optionally shaping the hydrogel of step a) in the form of a test sample hydrogel;
    c) submitting the hydrogel of step a) or of the optional step b) to a controlled shear strain application step and measuring the shear stress or measuring the shear strain;
    d) determining from the measured stress or strain of step c), the shear modulus of the hydrogel;
    e) determining the liquid content of the hydrogel ("test capacity") to be tested, or tested in step d), to determine the intrinsic gel strength of the water-absorbent hydrogel-forming polymer at the "test capacity";
    f) obtaining in step a) or in the optional step b) multiple hydrogels, comprising different water-absorbent polymeric material, having each a different chemical and/or physical property, and comprising a pre-determined amount of liquid ("test capacity"); and
    g) comparing the shear modulus values obtained in step d) for each hydrogel of step a), and/or the intrinsic gel strength obtained in step d) for each hydrogel of step a), to predict the influence of the difference in the chemical or physical property on the intrinsic gel strength.

2. The method according to claim 1, wherein step b) is performed.

3. The method according to claim 1, wherein the hydrogel of the water-absorbing polymeric material comprises at least about 50 g/g, of an aqueous liquid.

4. The method according to claim 3, wherein the hydrogel of the water-absorbing polymeric material comprises at least about 100 g/g, of an aqueous liquid.

5. The method according to claim 1, wherein the hydrogel is saturated with the liquid.

6. The method according to claim 5, wherein the liquid is a saline solution.

7. The method according to claim 1, wherein in step c) the hydrogel is obtained by swelling the water-absorbent hydrogel-forming polymeric material or a pre-cursor hydrogel to its equilibrium state in an aqueous liquid, to form the hydrogel of step a).

8. The method according to claim 7, wherein the polymeric material or a precursor-hydrogel is allowed to swell in the liquid for at least about 72 hours.

9. The method according to claim 8, wherein the polymeric material or a precursor-hydrogel is allowed to swell in the liquid for at least about a week.

10. The method according to claim 7, wherein the method step c) involves the use of a rheometer, applying a controlled oscillating shear strain or controlled oscillating shear stress.

11. The method according to claim 1, wherein the water-absorbent hydrogel-forming polymeric material comprises polyacrylate polymers, or derivatives thereof.

12. The method according to claim 1, wherein the step a) comprises the step of polymerizing monomers of the polymer in the presence of an aqueous liquid to obtain a hydrogel or hydrogel precursor.

13. The method according to claim 1, wherein the water-absorbent hydrogel-forming polymeric material comprises substantially no surface-crosslinking.

14. A method of predicting the absorbent behavior of a water-absorbent hydrogel-forming polymeric material, comprising inputting the intrinsic gel strength value obtained by the method described below into a model for predicting the absorbent behavior of a water-absorbent hydrogel-forming polymeric material, the method for determining the intrinsic gel strength of a water-absorbing hydrogel-forming polymeric material comprising the steps of:
- a) obtaining a hydrogel of the water-absorbing polymeric material, comprising at least about 5 g/g, of an aqueous liquid;
- b) optionally shaping the hydrogel of step a) in the form of a test sample hydrogel;
- c) submitting the hydrogel of step a) or of the optional step b) to a controlled shear strain application step and measuring the shear stress or measuring the shear strain; and
- d) determining from the measured stress or strain of step c), the shear modulus of the hydrogel.

15. A method for determining the intrinsic gel strength of a water-absorbent hydrogel-forming polymeric material, comprising the steps of:
- a) obtaining a hydrogel of the water-absorbent polymeric material, comprising at least about 5 g/g, of an aqueous liquid;
- b) optionally shaping the hydrogel of step a) in the form of a test sample hydrogel;
- c) applying a controlled uniaxial compression strain or stress to the hydrogel of step a) or of optional step b); and
- d) determining from the measured stress or strain of step c) the Young compression modulus of the hydrogel;
- e) determining the liquid content of the hydrogel ("test capacity") to be tested, or tested in step d), to determine the intrinsic gel strength of the water-absorbent hydrogel-forming polymer at the "test capacity";
- f) obtaining in step a) or in the optional step b) multiple hydrogels, comprising different water-absorbent polymeric material, having each a different chemical and/or physical property, and comprising a pre-determined amount of liquid ("test capacity"); and
- g) comparing the Young's compression modulus values obtained in step d) for each hydrogel of step a), and/or the intrinsic gel strength obtained in step d) for each hydrogel of step a), to predict the influence of the difference in the chemical or physical property on the intrinsic gel strength.

16. The method according to claim 15, wherein step b) is performed.

17. The method according to claim 15, wherein the hydrogel of the water-absorbing polymeric material comprises at least about 50 g/g, of an aqueous liquid.

18. The method according to claim 17, wherein the hydrogel of the water-absorbing polymeric material comprises at least about 100 g/g, of an aqueous liquid.

19. The method according to claim 15, wherein the hydrogel is saturated with the liquid.

20. The method according to claim 19, wherein the liquid is a saline solution.

21. The method according to claim 15, wherein in step c) the hydrogel is obtained by swelling the water-absorbent hydrogel-forming polymeric material or a pre-cursor hydrogel to its equilibrium state in an aqueous liquid, to form the hydrogel of step a).

22. The method according to claim 21, wherein the polymeric material or a precursor-hydrogel is allowed to swell in the liquid for at least about 72 hours.

23. The method according to claim 22, wherein the polymeric material or a precursor-hydrogel is allowed to swell in the liquid for at least about a week.

24. The method according to claim 15, wherein the water-absorbent hydrogel-forming polymeric material comprises polyacrylate polymers, or derivatives thereof.

25. The method according to claim 15, wherein the step a) comprises the step of polymerizing monomers of the polymer in the presence of an aqueous liquid to obtain a hydrogel or hydrogel precursor.

26. The method according to claim 15, wherein the water-absorbent hydrogel-forming polymeric material comprises substantially no surface-crosslinking.

27. A method of predicting the absorbent behavior of a water-absorbent hydrogel-forming polymeric material, comprising inputting the intrinsic gel strength value obtained by the method described below into a model for predicting the absorbent behavior of a water-absorbent hydrogel-forming polymeric material, the method for determining the intrinsic gel strength of a water-absorbent hydrogel-forming polymeric material comprising the steps of:
- a) obtaining a hydrogel of the water-absorbent polymeric material, comprising at least about 5 g/g, of an aqueous liquid;
- b) optionally shaping the hydrogel of step a) in the form of a test sample hydrogel;
- c) applying a controlled uniaxial compression strain or stress to the hydrogel of step a) or of optional step b); and
- d) determining from the measured stress or strain of step c) the Young compression modulus of the hydrogel.

* * * * *